United States Patent [19]
Ueda et al.

[11] Patent Number: 4,692,444
[45] Date of Patent: Sep. 8, 1987

[54] 1,4-DIHYDRO[1]BENZOTHIOPYRANO[4,3-c]PYRAZOLE DERIVATIVES, COMPOSITIONS CONTAINING THEM, AND PHARMACOLOGICAL METHODS OF USING THEM

[75] Inventors: Ikuo Ueda, Uenohigashi; Youichi Shiokawa, Ibaraki; Takashi Manabe, Kawanishi; Yousuke Katsura, Uenonishi, all of Japan

[73] Assignee: Fujisawa Pharmaceutical Co., Ltd., Osaka, Japan

[21] Appl. No.: 836,402

[22] Filed: Mar. 5, 1986

[30] Foreign Application Priority Data

Mar. 26, 1985 [GB] United Kingdom ............... 8507782

[51] Int. Cl.$^4$ ............... A61K 31/415; C07D 495/04
[52] U.S. Cl. ............... 514/406; 514/403; 548/370
[58] Field of Search ............... 548/370; 514/403, 406

[56] References Cited

U.S. PATENT DOCUMENTS

| | | | |
|---|---|---|---|
| 3,624,102 | 11/1971 | Brown et al. | 548/370 |
| 3,816,438 | 6/1974 | Houlihan | 548/370 |
| 3,963,740 | 6/1976 | Elslager | 548/370 |
| 4,026,899 | 5/1977 | Elslager | 548/370 |
| 4,335,134 | 6/1982 | Maurer et al. | 548/370 |

OTHER PUBLICATIONS

Mandal, Indian J. Chem., 1984, 23B(8), pp. 736-742.
Remington's Pharmaceutical Sciences, 14th edit., 1970, pp. 528-529.
*Protective Groups in Organic Chemistry*, McOmie edit., 1976, pp. 183-186.
*Advanced Organic Chemistry*, Mar., 2nd ed., 1977, p. 1125.

*Primary Examiner*—Henry R. Jiles
*Assistant Examiner*—Kurt G. Briscoe
*Attorney, Agent, or Firm*—Oblon, Fisher, Spivak, McClelland, & Maier

[57] ABSTRACT

This invention provides a benzene-fused heterocyclic compound of the formula:

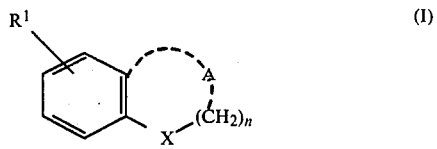

wherein
R$^1$ is halogen, nitro, amino, hydroxy, lower alkyl, lower alkoxy or acylamino,
X is —S—,

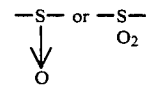

n is an integer of 1 or 2 and
A is a group of the formula:

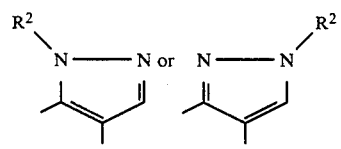

in which
R$^2$ is hydrogen, lower alkyl, lower alkynyl, carboxy(lower)alkyl or protected carboxy(lower)alkyl, or pharmaceutically acceptable salts thereof. This compound possesses diuretic, uricosuric, and vasodilative activities and therefore is useful as a diuretic agent, uricosuric agent and anti-hypertensive agent. This invention further provides processes for the preparation of this compound and pharmaceutical composition comprising compound of the above formula.

17 Claims, No Drawings

1,4-DIHYDRO[1]BENZOTHIOPYRANO[4,3-c]PYRAZOLE DERIVATIVES, COMPOSITIONS CONTAINING THEM, AND PHARMACOLOGICAL METHODS OF USING THEM

This invention relates to a new benzene-fused heterocyclic compound and pharmaceutically acceptable salt thereof.

More particularly, it relates to a new benzene-fused heterocyclic compound and pharmaceutically acceptable salt thereof which have diuretic activity, uricosuric activity and vasodilative activity, to processes for preparing thereof and to a pharmaceutical composition comprising the same.

The objective benzene-fused heterocyclic compound can be represented by the following formula:

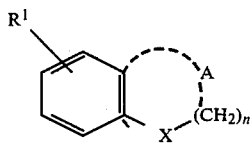

wherein
$R^1$ is halogen, nitro, amino, hydroxy, lower alkyl, lower alkoxy or acylamino, more specifically chlorine, nitro, amino, hydroxy, methyl, methoxy or acetamido, and most specifically halogen
X is —S—,

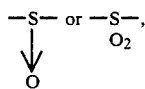

n is an integer of 1 or 2 and
A is a group of the formula:

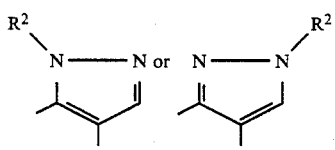

in which
$R^2$ is hydrogen, lower alkyl, lower alkynyl, carboxy(lower)alkyl, more specifically hydrogen, methyl, isopropyl, propargyl, carboxymethyl or ethoxycarbonylmethyl, and most specifically hydrogen or lower alkyl or protected carboxy(lower)alkyl.

The object compound (I) of this invention includes tautomeric isomers. That is, in case that the symbol "$R^2$" in the object compound (I) is hydrogen, said object compound (I) can be represented by the following tautomeric equilibrium.

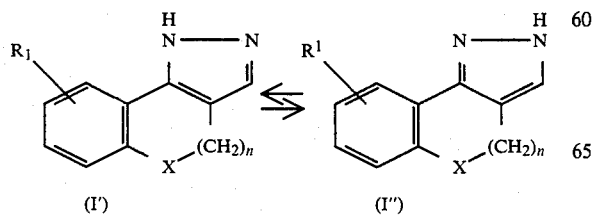

This type of tautomerism as stated above is well known, and it is obvious to any person skilled in the art that the both tautomeric isomers are easily convertible reciprocally and are included within the category of the same compound.

Accordingly, the both tautomeric isomers are clearly included within the scope of the object compound (I) of this invention. In the present specification and claims, said object compound (I) including both tautomeric isomers is represented by using the one of expressions; namely, the formula (I') only for the convenience' sake.

Suitable pharmaceutically acceptable salt of the object compound (I) are conventional non-toxic salts and may include a metal salt such as an alkali metal salt (e.g., sodium salt, potassium salt, etc.) and an alkaline earth metal salt (e.g., calcium salt, magnesium salt, etc.), ammonium salt, an organic amine salt (e.g., trimethylamine salt, triethylamine salt, pyridine salt, picoline salt, dicyclohexylamine salt, N.N'-dibenzylethylenediamine salt, etc.), an organic acid salt (e.g., acetate, maleate, tartrate, methanesulfonate, benzenesulfonate, toluenesulfonate, etc.), an inorganic acid salt (e.g., hydrochloride, hydrobromide, sulfate, phosphate, etc.), or a salt with an amino acid (e.g., arginine, aspartic acid, glutamic acid, etc.), and the like.

According to this invention, the new benzene-fused heterocyclic compound (I) and pharmaceutically acceptable salt thereof can be prepared by, for example, the following processes.

Process 1:

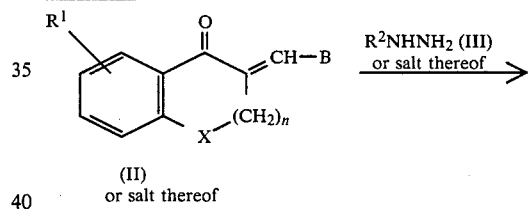

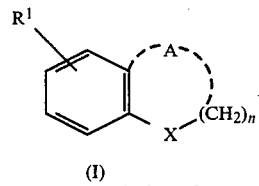

Process 2:

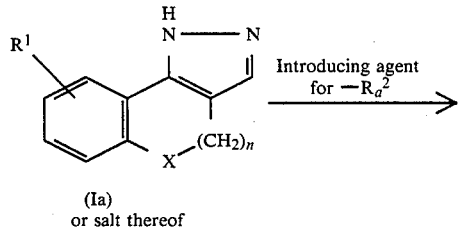

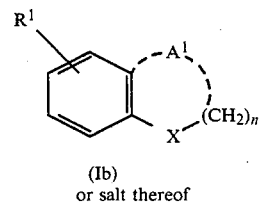

Process 3:

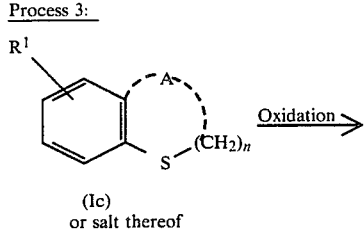

(Ic)
or salt thereof

Oxidation →

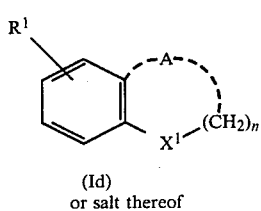

(Id)
or salt thereof

Process 4:

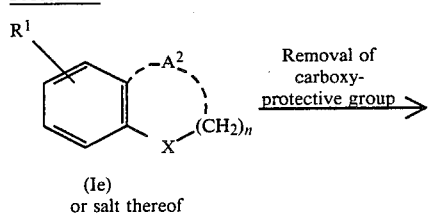

(Ie)
or salt thereof

Removal of carboxy-protective group →

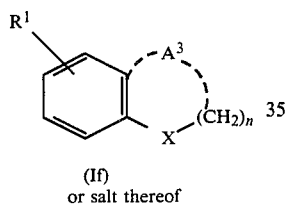

(If)
or salt thereof

Process 5:

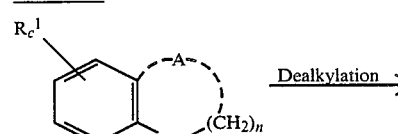

(Ig)
or salt thereof

Reduction →

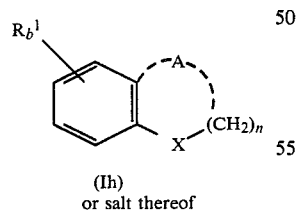

(Ih)
or salt thereof

Process 6:

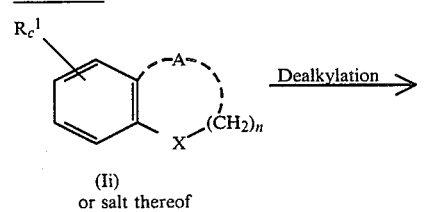

(Ii)
or salt thereof

Dealkylation →

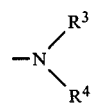

(Ij)
or salt thereof wherein
R¹, R², X, n and A are each as defined above,
$R_a^1$ is nitro,
$R_b^1$ is amino,
$R_c^1$ is lower alkoxy,
$R_d^1$ is hydroxy,
$R_a^2$ is lower alkyl, lower alkynyl, carboxy(lower)alkyl or protected carboxy(lower)alkyl,
$A^1$ is a group of the formula:

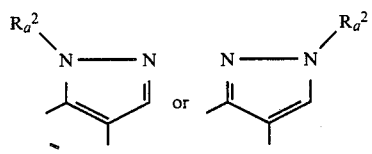

in which
$R_a^2$ is as defined above,
$A^2$ is a group of the formula:

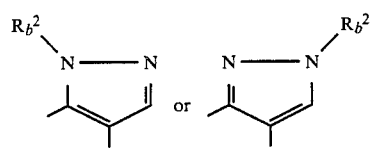

in which
$R_b^2$ is a protected carboxy(lower)alkyl,
$A^3$ is a group of the formula:

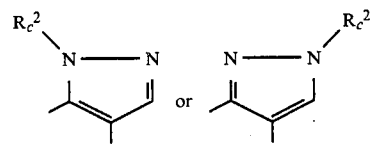

in which
$R_c^2$ is carboxy(lower)alkyl,
$X^1$ is

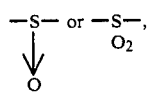

and
B is hydroxy or a group of the formula:

$$-N{\overset{R^3}{\underset{R^4}{}}}$$

in which $R^3$ and $R^4$ are each lower alkyl.

The starting compound (II) or salt thereof is a new compound and can be prepared by, for example, the following preparation and in a similar manner thereto.

Preparation $$\underset{\text{(IV) or salt thereof}}{R^1\text{—}\underset{X^{(CH_2)_n}}{\bigcirc}\text{—}CO\text{—}CH_2\text{—}} + \underset{\substack{\text{(V) or} \\ \text{lower alkyl formate}}}{R^3R^4N\text{—}CH(OR^5)(OR^6)} \longrightarrow \underset{\text{(II) or salt thereof}}{R^1\text{—}\underset{X^{(CH_2)_n}}{\bigcirc}\text{—}CO\text{—}CH=CH\text{—}B}$$

wherein $R^1$, $R^3$, $R^4$, X, n and B are each as defined above, and $R^5$ and $R^6$ are each lower alkyl.

The salts of compounds (Ia), (Ib), (Ic), (Id), (Ie), (If), (Ig), (Ih), (Ii) and (Ij) are the same as those exemplified for the pharmaceutically acceptable salt of the object compound (I) mentioned above.

The salts of the compounds (II), (III) and (IV) are the same acid salt as those exemplified for the pharmaceutically acceptable salt of the object compound (I) mentioned above.

In the above and subsequent descriptions of this specification, suitable examples and illustrations of the various definitions are explained in detail in the followings.

The term "lower" is intended to mean 1 to 6 carbon atom(s), unless otherwise indicated.

"Halogen" may include fluorine, chlorine, bromine and iodine.

Suitable "lower alkyl" in the terms "lower alkyl", "carboxy(lower)alkyl" and "protected carboxy(lower)alkyl" may include methyl, ethyl, propyl, isopropyl, butyl, isobutyl, t-butyl, pentyl, hexyl and the like.

Suitable "lower alkoxy" may include methoxy, ethoxy, propoxy, isopropoxy, butoxy, isobutoxy, t-butoxy, pentyloxy, hexyloxy and the like.

The "acyl" moiety in the term "acylamino" may include the residue of organic acid such as organic carboxylic acid, organic sulfonic acid, organic carbamic acid, organic carbonic acid and the like.

The "acylamino" includes both of monoacylamino and diacylamino.

Suitable "acyl" may be lower alkanoyl (e.g. formyl, acetyl, propionyl, butyryl, isobutyryl, 3,3-dimethylbutyryl, valeryl, isovaleryl, pivaloyl and the like.

Suitable "lower alkynyl" having 2 to 6 carbon atoms may include ethynyl, propargyl, 2-butynyl, 2-hexynyl and the like.

Suitable "protected carboxy" in the term "protected carboxy(lower)alkyl" may include esterified carboxy such as lower alkoxycarbonyl (e.g. methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl) and the like.

Preferable embodiments of the object compound (I) are as follows.

Preferable embodiment of $R^1$ is halogen, nitro, amino, hydroxy, lower alkyl, lower alkoxy or acylamino (more preferably lower alkanoylamino); X is —S—, $$-S-\text{ or }-\underset{\underset{O}{\downarrow}}{S}-;$$
$$\phantom{xxxxxxxxxxx}O_2$$

n is an integer of 1 or 2 and $R^2$ is hydrogen, lower alkyl, lower alkynyl, carboxy(lower)alkyl or protected carboxy(lower)alkyl [more preferably esterified carboxy(lower)alkyl [most preferably lower alkoxycarbonyl(lower)alkyl]].

The processes and preparation as illustrated above are explained in more detail in the followings.

Process 1

The object compound (I) or salt thereof can be prepared by reacting the compound (II) or salt thereof with the compound (III) or salt thereof.

This reaction is usually carried out in a solvent which does not adversely influence the reaction such as methanol, ethanol, propanol, tetrahydrofuran, chloroform, acetic acid and the like.

The reaction temperature is not critical and the reaction can be carried out under heating to under cooling.

In this reaction, if desired, the nitrogen atom of the compound (III) may be protected with a conventional amino-protective group (e.g. t-butoxycarbonyl). This case is also included within the scope of this process.

Process 2

The compound (Ib) or salt thereof can be prepared by reacting the compound (Ia) or salt thereof with an introducing agent for $-R_a^2$.

The preferred introducing agent for $-R_a^2$ is a compound of the formula : $R_a^2Y$ wherein $R_a^2$ is the same as defined above and Y is an acid residue such as halogen.

This reaction is usually carried out in a solvent which does not adversely influence the reaction such as N,N-dimethylformamide, dimethylsulfoxide, tetrahydrofuran and the like.

The reaction can preferably be conducted in the presence of an organic or inorganic base such as alkali metal (e.g. sodium), alkaline earth metal (e.g. calcium), alkali or alkaline earth metal hydride (e.g. sodium hydride, calcium hydride, etc.), alkali or alkaline earth metal hydroxide (e.g. sodium hydroxide, potassium hydroxide, calcium hydroxide, etc.), alkali or alkaline earth metal carbonate or bicarbonate (e.g. sodium carbonate, potassium carbonate, sodium bicarbonate), alkali or alkaline earth metal alkoxide (e.g. sodium ethoxide, lithium methoxide, magnesium methoxide), trialkylamine (e.g. triethylamine), pyridine, bicyclodiaza compound (e.g. 1,5-diazabicyclo[3,4,0]nonene-5, 1,5-diazabicyclo[5,4,0]undecene-5, etc.) and the like.

The reaction temperature is not critical and the reaction can be carried out under cooling to under heating.

Process 3

The compound (Id) or salt thereof can be prepared by oxidizing the compound (Ic) or salt thereof.

The oxidation is usually carried out by using an oxidizing agent employed for oxidizing an sulfur atom in heterocyclic ring (e.g. m-chloroperbenzoic acid, hydrogen peroxide, etc.).

When the equimolar of the oxidizing agent to the starting compound (Ic) or salt thereof is used, there is mainly given the sulfoxide (Id).

When 2 or more moles of the oxidizing agent to the starting compound (Ic) or salt thereof is used, there is mainly given the sulfone (Id).

The reaction of this process is usually carried out in a solvent which does not adversely influence the reaction such as methanol, ethanol, propanol, tetrahydrofuran, chloroform, dichloromethane and the like.

The reaction temperature is not critical and the reaction can be carried out under warming to cooling.

Process 4

The compound (If) or salt thereof can be prepared by subjecting the compound (Ie) or salt thereof to removal reaction of carboxy-protective group.

The removal reaction of this process may include hydrolysis, reduction and the like.

The hydrolysis is preferably carried out in the presence of inorganic or organic acid (e.g. hydrochloric acid, sulfuric acid, acetic acid, trifluoroacetic acid, etc.), or inorganic or organic base (e.g. sodium hydroxide, etc.).

The reaction of this process is usually carrried out in a solvent which does not adversely influence the reaction such as water, methanol, ethanol, propanol, acetic acid and the like, at a temperature range of cooling to heating.

Process 5

The compound (Ih) or salt thereof can be prepared by reducing the compound (Ig) or salt thereof.

The reduction is carried out in a conventional manner such as a reduction using a reducing agent (e.g. combination of iron and ammonium chloride, etc.), catalytic reduction and the like.

The reduction is usually carried out in a solvent which does not adversely influence the reaction such as water, ethanol, propanol, isobutyl alcohol, N,N-dimethylformamide, tetrahydrofuran, chloroform and the like, at a temperature range of cooling to heating.

Process 6

The compound (Ij) or salt thereof can be prepared by subjecting the compound (Ii) or salt thereof to dealkylation reaction.

The reaction is preferably carried out in the presence of a Lewis acid (e.g. boron trichloride, boron tribromide, etc.), hydrobromic acid, hydriodic acid and the like.

The reaction is usually carried out without a solvent or in a solvent which does not adversely influence the reaction such as chloroform, methylene chloride, carbon tetrachloride and the like.

The reaction temperature is not critical, and the reaction is usually carried out under cooling to under heating.

Preparation

The compound (II) or salt thereof can be prepared by reacting the compound (IV) or salt thereof with the compound (V) or lower alkyl formate.

The compound (IV) includes known compounds and novel ones. The known compounds, e.g. 6-chloro-2,3-dihydro-4H-1-benzothiopyran-4-one can be prepared by the method described in Yakugakuzasshi 81, 1(1961) and other compounds can also be prepared in a similar manner thereto.

This reaction is usually carried out in a solvent which does not adversely influence the reaction such as benzene, toluene, xylene, chloroform and the like.

This reaction can preferably be carried out in the presence of an inorganic or organic base such as those exemplified in the explanation of Process 2 mentioned above.

The reaction temperature is not critical and the reaction is preferably carried out under heating.

The object compounds of the above processes 1–6 and preparation can be purified and converted to the desired salts in a conventional manner.

The object compound (I) of this invention and pharmaceutically acceptable salt thereof possess diuretic activity, uricosuric activity and vasodilative activity. Accordingly, the object compound (I) is useful for a diuretic agent, uricosuric agent and anti-hypertensive agent.

For illustration purpose, some pharmacological data of the object compound (I) are shown in the followings.

Test 1 (Excretion of urine, electrolytes and uric acid in rats)

(1) Test compound

A compound of the formula:

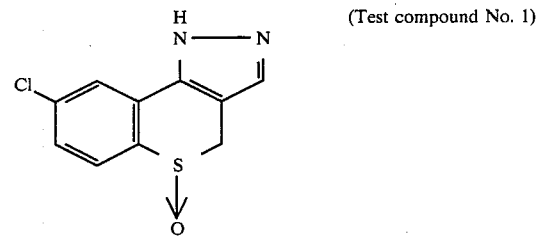

(Test compound No. 1)

(2) Test method

Male Jcl:SD strain rats aged 6-weeks were used after being deprived of food starving for 18 hours. The test compound was orally given to test rats (dosage: 320 mg/kg). Immediately after dosing, 20 ml/kg of physiological saline was given orally and animals were housed in a metabolism cage, and urine was collected at 3-hr intervals for 6 hrs. The experiments were conducted in 3 groups (3 rats/group) per test compound. Urine was measured with a measuring cylinder; urinary electrolytes($Na^+$ and $K^+$) with a Stat/Iron system (Technicon); and urinary uric acid by a modification of Makino's method using a kit (Determiner UA, sold by Kyowa Medex. Co.). All parameters were expressed as excretion values (%) per kg of body weight in comparison with those of the control rats.

(3) Test result

| Administered Test compound | Volume of urine (%) | Excretion of $Na^+$ (%) | Excretion of $K^+$ (%) | Excretion of uric acid (%) | $Na^+/K^+$ |
|---|---|---|---|---|---|
| — (control) | 100 | 100 | 100 | 100 | 1.00 |
| 1 | 276 | 480 | 383 | 206 | 1.24 |

The object compound (I) or its pharmaceutically acceptable salt can usually be administered to mammals including human beings in the form of a conventional pharmaceutical composition such as capsule, microcapsule, tablet, granule, powder, troche, syrup, aerosol, inhalation, solution, injection, suspension, emulsion, suppository, ointment, or the like.

The pharmaceutical composition of this invention can contain various organic or inorganic carrier materials, which are conventionally used for pharmaceutical purpose, such as excipient (e.g. sucrose, starch, mannit, sorbit, lactose, glucose, cellulose, talc, calcium phosphate, calcium carbonate, etc.), binding agent (cellulose, methylcellulose, hydroxypropylcellulose, polypropylpyrrolidone, gelatin, gum arabic, polyethyleneglycol, sucrose, starch, etc.), disintegrator (e.g. starch, carboxymethylcellulose, calcium salt of carboxymethylcellulose, hydroxypropylstarch, sodium glycolestarch, sodium bicarbonate, calcium phosphate, calcium citrate, etc.), lubricant (e.g. magnesium stearate, talc, sodium laurylsulfate, etc.), flavoring agent (e.g. citric acid, mentol, glycine, orange powders, etc.), preservative (sodium benzoate, sodium bisulfite, methylparaben, propylparaben, etc.), stabilizer (citric acid, sodium citrate, acetic acid, etc.), suspending agent (e.g. methylcellulose, polyvinylpyrrolidone, aluminum stearate, etc.), dispersing agent, aqueous diluting agent (e.g. water), base wax (e.g. cacao butter, polyethyleneglycol, white petrolatum, etc.).

A dosage of the present active ingredient is to be varied depending on various factors such as weight and/or age of a patient and/or the kind of the diseases, and further the kind of administration route. In general, an effective dosage can be selected from a range of about 20–2000 mg/day for an oral route, about 2.5–250 mg/day for an intramuscular or intravenous injection. The total daily amount mentioned above may be divisionally given to the patient at the interval of 6–12 hours per day. Preferable single dose of the present active ingredient may be, for example, about 10–500 mg per tablet or capsule, about 1.25–250 mg per vial or ampoule, and so on.

The following Examples are given for the purpose of illustrating this invention.

EXAMPLE 1

(1) A solution of 6-chloro-2,3-dihydro-4H-1-benzothiopyran-4-one (30 g), N,N-dimethylformamide dimethyl acetal (80 ml), and triethylamine (31.4 ml) in benzene (400 ml) was refluxed with stirring for 1 hour and then about three-fourths of the solvent were distilled slowly at atmospheric pressure over a period of approximately 1 hour. Benzene (300 ml) was added to the reaction mixture and the solvent was distilled again. To the residue was added diethyl ether (150 ml) and the mixture was triturated to give 6-chloro-2,3-dihydro-3-dimethylaminomethylene-4H-1-benzothiopyran-4-one (34 g).

mp: 126° to 127° C.
IR (Nujol): 1630 cm$^{-1}$
NMR (CDCl$_3$, $\delta$): 3.16 (6H, s), 4.01 (2H, s), 7.26 (1H, s), 7.27 (1H, d, J=1.5 Hz), 7.63 (1H, s), and 8.10 (1H, d, J=1.5 Hz)

(2) A mixture of 6-chloro-2,3-dihydro-3-dimethylaminomethylene-4H-1-benzothiopyran-4-one (7 g), hydrazine hydrate (2.01 ml), and acetic acid (2.37 ml) in methanol (140 ml) was stirred at room temperature for 5 hours and then evaporated in vacuo. To the residue was added aqueous sodium bicarbonate and extracted with ethyl acetate. The extract was washed with water, dried over magnesium sulfate, and evaporated in vacuo. The residue solid was recrystallized from ethyl acetate to give 8-chloro-1,4-dihydro[1]benzothiopyrano[4,3-c]pyrazole (2.85 g).

mp.: 205° to 206° C.
IR (Nujol): 3155,3125, 3195 cm$^{-1}$
NMR (DMSO-d$_6$, $\delta$): 4.03 (2H, s), 7.17 (1H, d, J=1.5 Hz), 7.22 (1H, s), 7.35 and 7.57 (1H, singlet each), 12.90 and 13.25 (1H, broad singlet each)

EXAMPLE 2

(1) A solution of m-chloroperbenzoic acid (1.72 g) in dichloromethane (30 ml) was added dropwise to a solution of 8-chloro-1,4-dihydro[1]benzothiopyrano[4,3-c]pyrazole (2.00 g) in a mixture of dichloromethane (60 ml) and tetrahydrofuran (30 ml). The resulting solution was stirred at room temperature for 1 hour and evaporated in vacuo. The residue was treated with a mixture of saturated aqueous sodium hydrogen carbonate (100 ml) and ethyl acetate (40 ml) and the mixture was vigorously stirred for several minutes. The resulting powder was collected by filtration, washed with water, and recrystallized from ethanol to give 8-chloro-1,4-dihydro[1]benzothiopyrano[4,3-c]pyrazole 5-oxide (0.90 g) as slightly yellow prisms.

mp.: 221° to 222° C.
IR (Nujol): 3150, 1010 cm$^{-1}$
NMR (DMSO-d$_6$, $\delta$) : 4.33 (2H, s), 7.58 (1H, dd, J=8.5 Hz and 2 Hz), 7.83 (1H, d, J=8.5 Hz), 7.90 (1H, s) and 7.92 (1H, d, J=2 Hz)

(2) 8-Chloro-1,4-dihydro[1]benzothiopyrano[4,3-c]pyrazole 5,5-dioxide from 8-chloro-1,4-dihydro[1]benzothiopyrano[4,3-c]pyrazole 5-oxide in similar manner to that of Example 2 (1).

mp: 259° to 260° C. (recrystallized from a mixture of tetrahydrofuran and methanol)
IR (Nujol): 3255, 1305, 1150 cm$^{-1}$
NMR (DMSO-d$_6$, $\delta$): 4.72 (2H, s), 7.58 (1H, dd, J=8.5 Hz and 2.0 Hz), 7.85 (1H, s), 7.93 (1H, d, J=8.5 Hz) and 7.95 (1H, d, J=2.0 Hz)

EXAMPLE 3

Methyl iodide (4.03 ml) was added dropwise to a mixture of 8-chloro-1,4-dihydro[1]benzothiopyrano[4,3-c]pyrazole 5-oxide (10.15 g) and potassium carbonate (8.30 g) in N,N-dimethylformamide (185 ml) and the mixture was stirred at room temperature overnight. The mixture was evaporated in vacuo and the residue was extracted with chloroform after an addition of water. The extract was washed with water, dried over magnesium sulfate, and evaporated in vacuo. The residue was dissolved in chloroform and the solution was chromatographed on silica gel (780 g).

The first eluate with a mixture of toluene and ethyl acetate (1:1) was evaporated in vacuo and the residual solid was recrystallized from a mixture of n-hexane and ethyl acetate to give 8-chloro-1,4-dihydro-1-methyl[1]benzothiopyrano[4,3-c]pyrazole 5-oxide (1.27 g).

The second eluate with ethyl acetate was evaporated in vacuo and the residual solid was recrystallized from a mixture of n-hexane, ethyl acetate, and chloroform to give 8-chloro-2,4-dihydro-2-methyl[1]benzothiopyrano[4,3-c]pyrazole 5-oxide (6.10 g).

8-Chloro-1,4-dihydro-1-methyl[1]benzothiopyrano[4,3-c]pyrazole 5-oxide:

mp: 178° to 179° C. (recrystallized from a mixture of ethyl acetate and n-hexane)

IR (Nujol): 1040 cm$^{-1}$

NMR (DMSO-d$_6$, δ): 4.14 (3H, s), 4.27 (2H, s), 7.60 (1H, s), 7.69 (1H, dd, J=1.5, 8 Hz), 7.85 (1H, d, J=8 Hz) and 7.93 (1H, d, J=1.5 Hz)

8-Chloro-2,4-dihydro-2-methyl[1]benzothiopyrano[4,3-c]pyrazole 5-oxide:

mp: 180° to 182° C. (recrystallized from a mixture of ethyl acetate and n-hexane)

IR (Nujol): 1040 cm$^{-1}$

NMR (DMSO-d$_6$): 3.91 (3H, s), 4.14 (1H, d, J=15 Hz), 4.43 (1H, d, J=15 Hz), 7.54 (1H, dd, J=2, 8 Hz), 7.82 (1H, d, J=2 Hz), 7.83 (1H, s) and 7.83 (1H, d, J=8 Hz)

EXAMPLE 4

The following compound was prepared in a similar manner to that of Example 3.

8-Chloro-2,4-dihydro-2-propargyl[1]benzothiopyrano[4,3-c]pyrazole 5-oxide:

mp: 169° to 171° C. (recrystallized from a mixture of ethyl acetate and n-hexane)

IR (Nujol): 3140, 2097, 1011 cm$^{-1}$

NMR (CDCl$_3$, δ): 2.59 (1H, t, J=2.5 Hz), 4.00 (1H, d, J=14 Hz), 4.30 (1H, d, J=14 Hz), 4.98 (2H, d, J=2.5 Hz), 7.41 (1H, dd, J=2, 9 Hz), 7.68 (1H, s), 7.74 (1H, d, J=9 Hz) and 7.93 (1H, d, J=2 Hz)

EXAMPLE 5

(1) The following compound was prepared in a similar manner to that of Example 1 (1).

2,3-Dihydro-3-dimethylaminomethylene-6-methoxy 4H-1-benzothiopyran-4-one.

mp: 115° to 118° C.

IR (Nujol): 1632, 1525 cm$^{-1}$

NMR (CDCl$_3$, δ): 3.13 (6H, s), 3.78 (3H, s), 3.95 (2H, s), 6.83 (1H, d,d; J=2, 8 Hz), 7.12 (1H, d, J=8 Hz), 7.52–7.67 (2H, m)

(2) The following compound was prepared in a similar manner to that of Example 1 (2).

[-Methoxy-1,4-dihydro[1]benzothiopyrano[4,3-c]pyrazole.

mp: 125° to 127° C. (recrystallized from a mixture of ethyl acetate and n-hexane).

NMR (DMSO-d$_6$, δ): 3.80 (3H, s), 3.98 (2H, s), 6.77 (1H, d,d; J=3, 9 Hz), 7.26 (1H, d, J=9 Hz), 7.41 (1H, d, J=3 Hz), 7.60 (1H, b.s.), 12.97 (b.s.)
13.33 (b.s.) } (1H).

IR (Nujol): 3150, 3060 cm$^{-1}$

EXAMPLE 6

(1) The following compound was prepared in a similar manner to that of Example 1 (1).

2,3-Dihydro-3-dimethylaminomethylene-6-nitro-4H-1-benzothiopyran-4-one.

mp: 199° to 200° C.

IR (Nujol): 1620, 1565, 1330 cm$^{-1}$

NMR (DMSO-d$_6$, δ): 3.19 (6H, s), 4.21 (2H, s), 7.57 (1H, d, J=8 Hz), 7.63 (1H, s), 8.12 (1H, d,d; J=2, 8 Hz), 8.66 (1H, d, J=2 Hz)

(2) The following compound was prepared in a similar manner to that of Example 1 (2).

[-Nitro-1,4-dihydro[1]benzothiopyrano[4,3-c]pyrazole.

mp: 205° to 206° C. (recrystallized from a mixture of chloroform and methanol).

IR (Nujol): 3100, 1502, 1335 cm$^{-1}$

NMR (DMSO-d$_6$, δ): 4.18 (2H, s), 7.54 (1H, d, J=9 Hz), 7.67 (1H, s), 7.96 (1H, d,d; J=2, 9 Hz), 8.50 (1H, d, J=2 Hz), 13.22 (1H, b.s.).

EXAMPLE 7

(1) The following compound was prepared in a similar manner to that of Example 1 (1).

6-Acetamido-2,3-dihydro-3-dimethylaminomethylene-4H-1-benzothiopyran-4-one.

mp: 202° to 204° C. (recrystallized from a mixture of methanol and tetrahydrofuran).

IR (Nujol): 3300, 1673, 1628 cm$^{-1}$

NMR (DMSO-d$_6$, δ): 2.03 (3H, s), 3.15 (6H, s), 4.05 (2H, s), 7.18 (1H, d, J=8 Hz), 7.48 (1H, s), 7.70 (1H, d,d; J=2, 8 Hz), 8.02 (1H, d, J=2 Hz), 9.95 (1H, b.s.)

(2) The following compound was prepared in a similar manner to that of Example 1 (2).

8-Acetamido-1,4-dihydro[1]benzothiopyrano[4,3-c]pyrazole.

mp: 203° to 207° C. (decomp.)(recrystallized from aqueous ethanol).

IR (Nujol): 3160, 1660 cm$^{-1}$

NMR (DMSO-d$_6$, δ): 2.05 (3H, s), 3.97 (2H, s), 7.10–7.75 (3H, m), 7.88–8.22 (1H, m), 12.88 (b.s.)
13.45 (b.s.) } (1H).

EXAMPLE 8

(1) A solution of 8-chloro-2,3-dihydro-4H-1-benzothiopyran-4-one (10 g) in benzene (125 ml) was added dropwise to a mixture of ethyl formate (7.46 g) and sodium methoxide (5.44 g) in benzene (40 ml) with ice cooling and stirring over a period of 10 minutes. After being stirred for 1 hour at room temperature, 10% hydrochloric acid was added to the reaction mixture. The aqueous layer was separated and extracted with ethyl acetate. The combined organic layers were washed with water, dried over magnesium sulfate, and evaporated in vacuo. The residue was recrystallized from a mixture of ethyl acetate and n-hexane to give 8-chloro-2,3-dihydro-3-hydroxymethylene-4H-1-benzothiopyran-4-one (10.13 g).

mp: 97° to 99° C.

IR (Nujol): 1630, 1575 (broad) cm$^{-1}$

NMR (CDCl$_3$, δ): 3.68 (2H, s), 7.03–7.63 (2H, m), 7.93 (1H, d,d; J=2, 8 Hz), 8.43 (1H, s), 14.68 (1H, b.s.).

(2) The following compound was prepared in a similar manner to that of Example 1 (2).

6-Chloro-1,4-dihydro[1]benzothiopyrano[4,3-c]pyrazole.

mp: 167° to 170° C. (recrystallized from a mixture of ethyl acetate and n-hexane).

IR (Nujol): 3080 (broad) cm$^{-1}$

NMR (DMSO-d$_6$, δ): 4.17 (2H, s), 7.03–7.48 (2H, m), 7.67 (1H, s), 7.83 (1H, d,d; J=2, 7 Hz), 13.08 (1H, b.s.).

EXAMPLE 9

(1) The following compound was prepared in a similar manner to that of Example 8 (1).

7-Chloro-2,3-dihydro-3-hydroxymethylene-4H-1-benzothiopyran-4-one.

mp: 101° to 103° C. (recrystallized from a mixture of ethyl acetate and n-hexane).

IR (Nujol): 1580 cm$^{-1}$

NMR (CDCl$_3$, δ): 3.65 (2H, s), 7.12 (1H, d,d; J=2, 8 Hz), 7.42 (1H, d, J=2 Hz), 7.83 (1H, d, J=8 Hz), 8.28 (1H, s), 14.60 (1H, b.s.)

(2) The following compound was prepared in a similar manner to that of Example 1 (2).

7-Chloro-1,4-dihydro[1]benzothiopyrano[4,3-c]pyrazole.

mp: 198.5° to 203° C. (recrystallized from a mixture of ethyl acetate and n-hexane).

IR (Nujol): 3125, 3075 cm$^{-1}$

NMR (DMSO-d$_6$, δ): 4.08 (2H, s), 7.23 (1H, d,d; J=2, 8 Hz), 7.40 (1H, d, J=2 Hz), 7.60 (1H, s), 7.78 (1H, d, J=8 Hz), 13.03 (1H, b.s.).

EXAMPLE 10

(1) The following compound was prepared in a similar manner to that of Example 8 (1).

2,3-Dihydro-3-hydroxymethylene-6-methyl-4H-1-benzothiopyran-4-one.

mp: 88° to 90° C. (recrystallized from a mixture of ethyl acetate and n-hexane).

IR (Nujol): 1600 (broad) cm$^{-1}$

NMR (CDCl$_3$, δ): 2.35 (3H, s), 3.63 (2H, s), 7.18 (2H, b.s.), 7.80 (1H, s), 8.35 (1H, s), 14.83 (1H, b.s.)

(2) The following compound was prepared in a similar manner to that of Example 1 (2).

[-Methyl-1,4-dihydro[1]benzothiopyrano[4,3-c]pyrazole.

mp: 171° to 174° C. (recrystallized from a mixture of ethyl acetate and n-hexane).

IR (Nujol ): 3200, 3170 cm$^{-1}$

NMR (DMSO-d$_6$, δ): 2.28 (3H, s), 3.88 (2H, s), 6.98 (1H, d,d; J=2, 8 Hz), 7.21 (1H, d, J=8 Hz), 7.40–7.74 (2H, m), 12.87 (b.s.) ⎫
13.27 (b.s.) ⎭ (1H)

EXAMPLE 11

(1) The following compound was prepared in a similar manner to that of Example 8 (1).

7-Chloro-4-hydroxymethylene-5-oxo-2,3,4,5-tetrahydro-1-benzothiepin.

mp: 118° to 120° C. (recrystallized from a mixture of ethyl acetate and n-hexane).

IR (Nujol): 1620 cm$^{-1}$

NMR (CDCl$_3$, δ): 2.38 (2H, t, J=6 Hz), 3.18 (2H, t, J=6 Hz), 7.17–7.73 (3H, m), 7.92–8.28 (1H, b.s.), 14.42 (1H, b.s.).

(2) The following compound was prepared in a similar manner to that of Example 1 (2).

9-Chloro-4,5-dihydro-1H-[1]benzothiepino[5,4-c]pyrazole.

mp: 152° to 153° C. (recrystallized from a mixture of ethyl acetate and n-hexane).

IR (Nujol): 3100 cm$^{-1}$

NMR (DMSO-d$_6$, δ): 3.10 (4H, b.s.), 7.13–8.03 (4H, m), 13.09 (1H, b.s.)

EXAMPLE 12

(1) A solution of 6-chloro-2,3-dihydro-3-dimethylaminomethylene-4H-1-benzothiopyran-4-one (34.13 g), 1-t-butoxycarbonyl-1-methylhydrazine (59.14 g), and acetic acid (23.14 ml) in methanol (2 l) and tetrahydrofuran (1 l) was stirred at ambient temperature for 6 hours and then evaporated in vacuo. To the residue was added aqueous sodium bicarbonate and the mixture was extracted with ethyl acetate. The extract was washed with water, dried over magnesium sulfate, and evaporated in vacuo to give 3-(2-t-butoxycarbonyl-2-methylhydrazinomethylene)-6-chloro-2,3-dihydro-4H-1-benzothiopyran-4-one (61.65 g).

mp: 121° to 124° C. (recrystallized from a mixture of ethyl acetate and benzene).

IR (Nujol): 1680, 1617 cm$^{-1}$

NMR (CDCl$_3$, δ): 1.50 (9H, s), 3.20 (3H, s), 3.60 (2H, s), 7.02 (1H, d, J=6 Hz), 7.12–7.35 (2H, m), 7.78–8.02 (1H, m), 11.63 (1H, d, J=6 Hz).

(2) A solution of hydrogen chloride in methanol (225 ml) was added to a suspension of 3-(2-t-butoxycarbonyl-2-methylhydrazinomethylene)-6-chloro-2,3-dihydro-4H-1-benzothiopyran-4-one (54.14 g) in methanol (550 ml). After being stirred at ambient temperature for 8 hours, the mixture was evaporated in vacuo and the residue was extracted with ethyl acetate after an addition of water. The extract was washed with aqueous sodium bicarbonate and then water, dried over magnesium sulfate, and evaporated in vacuo to give 8-chloro-1-methyl-1,4-dihydro[1]benzothiopyrano[4,3-c]pyrazole (26.63 g).

NMR (CDCl$_3$, δ): 3.83 (2H, s), 4.12 (3H, s), 7.18 (1H, d,d; J=2, 8 Hz), 7.36 (1H,s), 7.43 (1H, d, J=9 Hz), 7.58 (1H, d, J=2 Hz)

EXAMPLE 13

The following compounds were prepared in a similar manner to that of Example 3.

(1) 8-Chloro-2-ethoxycarbonylmethyl-2,4-dihydro[1]benzothiopyrano[4,3-c]pyrazole 5-oxide.

mp: 121.5° to 123° C. (recrystallized from a mixture of ethyl acetate and n-hexane).

IR (Nujol): 1611, 1035 cm$^{-1}$

NMR (CDCl$_3$, δ): 1.29 (3H, t, J=7.5 Hz), 4.04 (1H, d, J=15 Hz), 4.25 (2H, q, J=7.5 Hz), 4.29 (1H, d, J=15 Hz), 4.91 (2H, s), 7.42 (1H, d,d; J=2, 8 Hz), 7.51 (1H, s), 7.74 (1H, d, J=8 Hz), 7.91 (1H, d, J=2 Hz).

(2) 8-Chloro-2-isopropyl-2,4-dihydro[1]benzothiopyrano[4,3-c]pyrazole.

IR (film): 1670 cm$^{-1}$

NMR (CDCl$_3$, δ): 1.53 (6H, d, J=7 Hz), 3.90 (2H, s), 4.47 (1H, septet, J=7 Hz), 6.87–7.43 (3H, m), 7.77–8.03 (1H, m).

(3) 8-Chloro-1-isopropyl-1,4-dihydro[1]benzothiopyrano[4,3-c]pyrazole.

IR (film): 1666 cm$^{-1}$ NMR (CDCl$_3$, δ): 1.60 (6H, d, J=6 Hz), 3.78 (2H, s), 4.83 (1H, septet, J=6 Hz), 6.98–7.70 (4H, m)

EXAMPLE 14

The following compounds were prepared in a similar manner to that of Example 2.

(1) 8-Chloro-2-isopropyl-2,4-dihydro[1]benzothiopyrano[4,3-c]pyrazole 5-oxide.

mp: 111° to 113° C. (recrystallized from a mixture of ethyl acetate and n-hexane).

IR (Nujol): 1043 cm$^{-1}$

NMR (CDCl$_3$, δ): 1.53 (6H, d, J=6.5 Hz), 4.02 (1H, d, J=15 Hz), 4.26 (1H, d, J=15 Hz), 4.51 (1H, septet, J=6.5 Hz), 7.43 (1H, d,d; J=2, 8 Hz), 7.54 (1H, s), 7.71 (1H, d, J=8 Hz), 7.93 (1H, d, J=2 Hz).

(2) 6-Chloro-1,4-dihydro[1]benzothiopyrano[4,3-c]pyrazole 5-oxide.

mp: 233° to 235° C. (decomp.)(recrystallized from aqueous ethanol).

IR (Nujol): 3130, 1580, 1010 cm$^{-1}$

NMR (DMSO-d$_6$, δ): 4.03 (1H, d, J=16 Hz), 4.58 (1H, d, J=16 Hz), 7.35-8.27 (4H, m), 13.30 (1H, b.s.).

(3) 7-Chloro-1,4-dihydro[1]benzothiopyrano[4,3-c]pyrazole 5-oxide.

mp: 214° to 215° C. (decomp.)(recrystallized from aqueous ethanol).

IR (Nujol): 3120 (broad), 1026 cm$^{-1}$

NMR (DMSO-d$_6$, δ): 4.33 (2H, s), 7.50-8.08 (4H, m), 13.22 (1H, b.s.).

(4) 8-Methyl-1,4-dihydro[1]benzothiopyrano[4,3-c]pyrazole 5-oxide.

mp: 222° to 223° C. (decomp.)(recrystallized from ethanol).

IR (Nujol): 3080, 1582, 990 cm$^{-1}$

NMR (DMSO-d$_6$, δ): 2.42 (3H, s), 4.06 (1H, d, J=15 Hz), 4.36 (1H, d, J=15 Hz), 7.20-7.48 (1H, m), 7.60-7.95 (3H, m), 13.13 (1H, b.s.).

(5) 8-Methyl-1,4-dihydro[1]benzothiopyrano[4,3-c]pyrazole 5,5-dioxide.

mp: 240° to 242° C. (recrystallized from methanol).

IR (Nujol): 3200, 1598, 1297, 1150 cm$^{-1}$

NMR (DMSO-d$_6$, δ): 2.47 (3H, s), 4.67 (2H, s), 7.25-7.50 (1H, m), 7.65-7.98 (3H, m), 13.32 (1H, b.s.).

(6) 8-Methoxy-1,4-dihydro[1]benzothiopyrano[4,3-c]pyrazole 5-oxide.

mp: 217° to 218° C. (recrystallized from a mixture of methanol and tetrahydrofuran).

IR (Nujol): 3100 (broad), 1010 cm$^{-1}$

NMR (DMSO-d$_6$, δ): 3.86 (3H, s), 4.03 (1H, d, J=16 Hz), 4.36 (1H, d, J=16 Hz), 7.06 (1H, d,d; J=2, 8 Hz), 7.49 (1H, d, J=2 Hz), 7.78 (1H, d, J=8 Hz), 7.83 (1H, s), 13.17 (1H, b.s.).

(7) 8-Hydroxy-1,4-dihydro[1]benzothiopyrano[4,3-c]pyrazole 5-oxide.

mp: 217° C. (decomp.)(recrystallized from aqueous ethanol).

IR (Nujol): 3225, 3090, 1030 cm$^{-1}$

NMR (DMSO-d$_6$, δ): 3.94 (1H, d, J=15 Hz), 4.34 (1H, d, J=15 Hz), 6.85 (1H, d,d; J=2, 8 Hz), 7.35 (1H, d, J=2 Hz), 7.63 (1H, d, J=8 Hz), 7.78 (1H, s), 10.27 (1H, b.s.), 13.07 (1H, b.s.).

(8) 8-Nitro-1,4-dihydro[1]benzothiopyrano[4,3-c]pyrazole 5-oxide.

mp: 206° to 208° C. (decomp.)(recrystallized from aqueous ethanol).

IR (Nujol): 3070, 1508, 1360, 1008 cm$^{-1}$

NMR (DMSO-d$_6$, δ): 4.43 (2H, s), 7.96 (1H, s), 8.05 (1H, d, J=9 Hz), 8.35 (1H, d,d; J=2, 9 Hz), 8.51 (1H, d, J=2 Hz), 13.40 (b.s.) ⎫
13.94 (b.s.) ⎬ (1H)

(9) 9-Chloro-4,5-dihydro-1H-[1]benzothiepino[5,4-c]-pyrazole 6-oxide.

mp: 176° to 178° C. (recrystallized from ethanol).

IR (Nujol): 3150, 1010 cm$^{-1}$

NMR (DMSO-d$_6$, δ): 2.80-3.83 (4H, m), 7.64 (1H, d,d; J=2, 8 Hz), 7.76 (1H, s), 7.80 (1H, d, J=8 Hz), 7.94 (1H, d, J=2 Hz), 13.27 (1H, b.s.).

(10) 9-Chloro-4,5-dihydro-1H-[1]benzothiepino[5,4-c]pyrazole 6,6-dioxide.

mp: 168° to 169° C. (recrystallized from ethanol).

IR (Nujol): 3170, 1280, 1120 cm$^{-1}$

NMR (DMSO-d$_6$, δ): 3.00-3.50 (2H, m), 3.60-4.03 (2H, m), 7.59 (1H, d,d; J=2, 9 Hz), 7.80 (1H, s), 8.06 (1H, d, J=9 Hz), 8.43 (1H, b.s.), 13.30 (1H, b.s.).

EXAMPLE 15

A mixture of 8-chloro-2-ethoxycarbonylmethyl-2,4-dihydro[1]benzothiopyrano[4,3-c]pyrazole 5-oxide (3 g) and 1N aqueous sodium hydroxide (9.25 ml) in methanol (90 ml) was stirred at ambient temperature for 30 minutes and then evaporated in vacuo. To the residue were added 1N hydrochloric acid and ethyl acetate, the insoluble material was collected by suction, and washed with water. The obtained crude product was recrystallized from a mixture of ethanol and n-hexane to give 2-carboxymethyl-8-chloro-2,4-dihydro[1]benzothiopyrano[4,3-c]pyrazole 5-oxide (0.78 g).

mp: 221.5° to 224.5° C. (decomp.)

IR (Nujol): 1700 cm$^{-1}$

NMR (DMSO-d$_6$, δ): 4.19 (1H, d, J=15 Hz), 4.41 (1H, d, J=15 Hz), 5.04 (2H, s), 7.40 (1H, d,d; J=2, 8 Hz), 7.80 (1H, d, J=2 Hz), 7.83 (1H, d, J=8 Hz), 7.88 (1H, s).

EXAMPLE 16

To a stirred mixture of iron powder (8.53 g) and ammonium chloride (0.85 g) in water (22 ml) and ethanol (66 ml) was added portionwise 8-nitro-1,4dihydro[1]benzothiopyrano[4,3-c]pyrazole (6.6 g) under reflux over a period of 15 minutes. After being stirred for 30 minutes under reflux, the mixture was filtered and the filtrate was evaporated in vacuo. To the residue were added aqueous sodium bicarbonate and ethyl acetate and the mixture was stirred at room temperature. The resulting precipitate was collected by filtration, washed with water, and recrystallized from a mixture of tetrahydrofuran and methanol to give 8-amino-1,4-dihydro[1]benzothiopyrano[4,3-c]pyrazole (3.79 g).

mp: 197° to 199° C.

IR (Nujol): 3370, 3200, 3080, 1600 cm$^{-1}$

NMR (DMSO-d$_6$, δ): 3.87 (2H, s), 5.07 (2H, b.s.), 6.43 (1H, d,d; J=2, 9 Hz), 6.83-7.27 (2H, m), 7.33-7.67 (1H, m), 12.03-13.47 (1H, b.s.).

EXAMPLE 17

A mixture of 8-methoxy-1,4-dihydro[1]benzothiopyrano[4,3-c]pyrazole (6.75 g) and 47% hydrobromic acid (70.2 ml) was refluxed for 3 hours with stirring and allowed to cool to room temperature. The resulting precipitate was collected by filtration and recrystallized from water to give the salt, which was treated with aqueous sodium bicarbonate to give 8-hydroxy-1,4dihydro[1]benzothiopyrano[4,3-c]pyrazole (4.73 g).

mp: 224° to 226° C.

IR (Nujol): 3240 cm$^{-1}$

NMR (DMSO-d$_6$, δ): 3.93 (2H, s), 6.67 (1H, d,d; J=2, 8 Hz), 7.17 (1H, d, J=8 Hz), 7.28 (1H, d, J=2 Hz), 7.53(1H, s), 9.43 (1H, s), 12.90 (1H, b.s.).

EXAMPLE 18

The following compounds were prepared in a similar manner to that of Example 1 (2).

(1) 8-Chloro-1,4-dihydro-1-methyl[1]benzothiopyrano[4,3-c]pyrazole 5-oxide

NMR (DMSO-d$_6$, δ): 4.14 (3H, s), 4.27 (2H, s), 7.60 (1H, s), 7.69 (1H, d,d; J=1.5, 8 Hz), 7.85 (1H, d, J=8 Hz) and 7.93 (1H, d, J=1.5 Hz).

(2) 8-Chloro-2,4-dihydro-2-methyl[1]benzothiopyrano[4,3-c]pyrazole 5-oxide

NMR (DMSO-d$_6$, δ): 3.91 (3H, s), 4.14 (1H, d, J=15 Hz), 4.43 (1H, d, J=15 Hz), 7.54 (1H; d,d; J=2, 8 Hz), 7.82 (1H, d, J=2 Hz), 7.83 (1H, s) and 7.83 (1H, d, J=8 Hz).

(3) 8-Chloro-2,4-dihydro-2-propargyl[1]benzothiopyrano[4,3-c]pyrazole 5-oxide

NMR (CDCl$_3$, δ): 2.59 (1H, t, J=2.5 Hz), 4.00 (1H, d, J=14 Hz), 4.30 (1H, d, J=14 Hz), 4.98 (2H, d, J=2.5 Hz), 7.41 (1H; d,d; J=2, 9 Hz), 7.68 (1H, s), 7.74 (1H, d, J=9 Hz) and 7.93 (1H, d, J=2 Hz).

(4) 8-Chloro-2-ethoxycarbonylmethyl-2,4-dihydro[1]benzothiopyrano[4,3-c]pyrazole 5-oxide.

NMR (CDCl$_3$, δ): 1.29 (3H, t, J=7.5 Hz), 4.04 (1H, d, J=15 Hz), 4.25 (2H, q, J=7.5 Hz), 4.29 (1H, d, J=15 Hz), 4.91 (2H, s), 7.42 (1H; d,d; J=2, 8 Hz), 7.51 (1H, s), 7.74 (1H, d, J=8 Hz), 7.91 (1H, d, J=2 Hz).

(5) 8-Chloro-2-isopropyl-2,4-dihydro[1]benzothiopyrano[4,3-c]pyrazole.

NMR (CDCl$_3$, δ): 1.53 (6H, d, J=7 Hz), 3.90 (2H, s), 4.47 (1H, septet, J=7 Hz), 6.87–7.43 (3H, m), 7.77–8.03 (1H, m).

(6) 8-Chloro-1-isopropyl-1,4-dihydro[1]benzothiopyrano[4,3-c]pyrazole

NMR (CDCl$_3$, δ): 1.60 (6H, d, J=6 Hz), 3.78 (2H, s), 4.83 (1H, septet, J=6 Hz), 6.98–7.70 (4H, m)

(7) 2-Carboxymethyl-8-chloro-2,4-dihydro[1]benzothiopyrano[4,3-c]pyrazole 5-oxide NMR (DMSO-d$_6$, δ): 4.19 (1H, d, J=5 Hz), 4.41 (1H, d, J=15 Hz), 5.04 (2H, s), 7.40 (1H; d,d; J=2, 8 Hz), 7.80 (1H, d, J=2 Hz), 7.83 (1H, d, J=8 Hz), 7.88 (1H, s).

(8) 8-Amino-1,4-dihydro[1]benzothiopyrano[4,3-c]pyrazole

NMR (DMSO-d$_6$, δ): 3.87 (2H, s), 5.07 (2H, b.s.), 6.43 (1H; d,d; J=2,9 Hz), 6.83–7.27 (2H, m), 7.33–7.67 (1H, m), 12.03–13.47 (1H, b.s.).

(9) 8-Hydroxy-1,4-dihydro[1]benzothiopyrano[4,3-c]pyrazole.

NMR (DMSO-d$_6$, δ): 3.93 (2H, s), 6.67 (1H; d,d; J=2, 8 Hz), 7.17 (1H, d, J=8 Hz), 7.28 (1H, d, J=2 Hz), 7.53 (1H, s), 9.43 (1H, s), 12.90 (1H, b.s.).

(10) 8-Chloro-1,4-dihydro[1]benzothiopyrano[4,3-c]pyrazole 5-oxide.

NMR (DMSO-d$_6$, δ): 4.33 (2H, s), 7.58 (1H; d,d; J=8.5, 2 Hz), 7.83 (1H, d, J=8.5 Hz), 7.90 (1H, s), 7.92 (1H, d, J=2 Hz).

(11) 8-Chloro-1,4-dihydro[1]benzothiopyrano[4,3-c]pyrazole 5,5-dioxide.

NMR (DMSO-d$_6$, δ): 4.72 (2H, s), 7.58 (1H; d,d; J=8.5, 2.0 Hz), 7.85 (1H, s), 7.93 (1H, d, J=8.5 Hz), 7.95 (1H, d, J=2.0 Hz).

(12) 8-Chloro-2-isopropyl-2,4-dihydro[1]benzothiopyrano[4,3-c]pyrazole 5-oxide.

NMR (CDCl$_3$, δ): 1.53 (6H, d, J=6.5 Hz), 4.02 (1H, d, J=1 5 Hz), 4.26 (1H, d, J=15 Hz), 4.51 (1H, septet, J=6.5 Hz), 7.43 (1H; d,d; J=2, 8 Hz), 7.54 (1H, s), 7.71 (1H, d, J=8 Hz), 7.93 (1H, d, J=2 Hz).

(13) 6-Chloro-1,4-dihydro[1]benzothiopyrano[4,3-c]pyrazole 5-oxide.

NMR (DMSO-d$_6$, δ): 4.03 (1H, d, J=16 Hz), 4.58 (1H, d, J=16 Hz), 7.35–8.27 (4H, m), 13.30 (1H, b.s.).

(14) 7-Chloro-1,4-dihydro[1]benzothiopyrano[4,3-c]pyrazole 5-oxide

NMR (DMSO-d$_6$, δ): 4.33 (2H, s), 7.50–8.08 (4H, m), 13.22 (1H, b.s.).

(15) 8-Methyl-1,4-dihydro[1]benzothiopyrano[4,3-c]pyrazole 5-oxide.

NMR (DMSO-d$_6$, δ): 2.42 (3H, s), 4.06 (1H, d, J=15 Hz), 4.36 (1H, d, J=15 Hz), 7.20–7.48 (1H, m), 7.60–7.95 (3H, m), 13.13 (1H, b.s.).

(16) 8-Methyl-1,4-dihydro[1]benzothiopyrano[4,3-c]pyrazole 5,5-dioxide

NMR (DMSO-d$_6$, δ): 2.47(3H, s), 4.67(2H, s), 7.25–7.50 (1H, m), 7.65–7.98 (3H, m), 13.32 (1H, b.s.).

(17) 8-Methoxy-1,4-dihydro[1]benzothiopyrano[4,3-c]pyrazole 5-oxide.

NMR (DMSO-d$_6$, δ): 3.86 (3H, s), 4.03 (1H, d, J=16 Hz), 4.36 (1H, d, J=16 Hz), 7.06 (1H; d,d; J=2, 8 Hz), 7.49 (1H, d, J=2 Hz), 7.78 (1H, d, J=8 Hz), 7.83 (1H, s), 13.17 (1H, b.s.).

(18) 8-Hydroxy-1,4-dihydro[1]benzothiopyrano[4,3-c]pyrazole 5-oxide.

NMR (DMSO-d$_6$, δ): 3.94 (1H, d, J=15 Hz), 4.34 (1H, d, J=15 Hz), 6.85 (1H; d,d; J=2, 8 Hz), 7.35 (1H, d, J=2 Hz), 7.63 (1H, d, J=8 Hz), 7.78 (1H, s), 10.27 (1H, b.s.), 13.07 (1H, b.s.)

(19) 8-Nitro-1,4-dihydro[1]benzothiopyrano[4,3-c]pyrazole

NMR (DMSO-d$_6$, δ): 4.43 (2H, s), 7.96 (1H, s), 8.05 (1H, d, J=9 Hz), 8.35 (1H; d,d; J=2, 9 Hz), 8.51 (1H, d, J=2 Hz), 13.40 (b.s.) ⎫
13.94 (b.s.) ⎭ (1H)

(20) 9-Chloro-4,5-dihydro-1H-[1]benzothiepino[5,4-c]pyrazole 6-oxide.

NMR (DMSO-d$_6$, δ): 2.80–3.83 (4H, m), 7.64 (1H, d,d; J=2, 8 Hz), 7.76 (1H, s), 7.80 (1H, d, J=8 Hz), 7.94 (1H, d, J=2 Hz), 13.27 (1H, b.s.).

(21) 9-Chloro-4,5-dihydro-1H-[1]-benzothiepino[5,4-c]pyrazole 6,6-dioxide.

NMR (DMSO-d$_6$, δ): 3.00–3.50 (2H, m), 3.60–4.03 (2H, m), 7.59 (1H; d,d; J=2, 9 Hz), 7.80 (1H, s), 8.06 (1H, d, J=9 Hz), 8.43 (1H, b.s.), 13.30 (1H, b.s.).

EXAMPLE 19

The following compounds were prepared in a similar manner to that of Example 3 (1).

(1) 8-Chloro-1-methyl-1,4-dihydro[1]benzothiopyrano[4,3-c]pyrazole.

NMR (CDCl$_3$, δ): 3.83 (2H, s), 4.12 (3H, s), 7.18 (1H; d,d; J=2, 9 Hz), 7.36 (1H, s), 7.43 (1H, d, J=9 Hz), 7.58 (1H, d, J=2 Hz).

(2) 8-Chloro-2-methyl-2,4-dihydro[1]benzothiopyrano[4,3-c]pyrazole.

NMR (CDCl$_3$, δ): 3.90 (5H, s), 7.12 (1H; d,d; J=2, 9 Hz), 7.19 (1H, s), 7.28 (1H, d, J=9 Hz), 7.91 (1H, d, J=2 Hz).

(3) 2-Carboxymethyl-8-chloro-2,4-dihydro[1]benzothiopyrano[4,3-c]pyrazole 5-oxide.

NMR (DMSO-d$_6$, δ): 4.19 (1H, d, J=15 Hz), 4.41 (1H, d, J=15 Hz), 5.04 (2H, s), 7.40 (1H; d,d; J=2, 8 Hz), 7.80 (1H, d, J=2 Hz), 7.83 (1H, d, J=8 Hz), 7.88 (1H, s)

EXAMPLE 20

A mixture of 6-chloro-2,3-dihydro-3-dimethylaminomethylene-4H-1-benzothiopyran-4-one (8 g), methylhydrazine (2.5 ml), and acetic acid (2.7 ml) in methanol (160 ml) was stirred at room temperature for 2 hours and then evaporated in vacuo. The residue was neutralized with aqueous sodium bicarbonate and extracted with ethyl acetate. The extract was washed with water, dried over magnesium sulfate, and evaporated in vacuo. The oily residue was chromatographed on silica gel (380 g) using toluene as an eluent.

The first eluate was evaporated in vacuo to give 8-chloro-2-methyl-2,4-dihydro[1]benzothiopyrano[4,3-c]pyrazole (3.4 g).

NMR (CDCl$_3$, δ): 3.90 (5H, s), 7.12 (1H; d,d; J=2, 9 Hz), 7.19 (1H, s), 7.28 (1H, d, J=9 Hz), 7.91 (1H, d, J=2 Hz).

The second eluate was evaporated in vacuo to give 8-chloro-1-methyl-1,4-dihydro[1]benzothiopyrano[4,3-c]pyrazole (1.0 g).

NMR (CDCl$_3$, δ): 3.83 (2H, s), 4.12 (3H, s), 7.18 (1H; d,d; J=2, 8 Hz), 7.36 (1H, s), 7.43 (1H, d, J=9 Hz), 7.58 (1H, d, J=2 Hz).

EXAMPLE 21

(Preparation of granules or small granules)

8-Chloro-1,4-dihydro[1]benzothiopyrano[4,3-c]pyrazole

| | |
|---|---|
| 5-oxide | 5000 (g) |
| Sucrose | 9250 |
| Hydroxypropylcellulose | 200 |
| Starch | 50 |

The above ingredients are blended and granulated or grained in a conventional manner into granules or small granules.

We claim:

1. A compound of the formula:

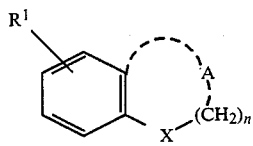

(I)

wherein R$^1$ is halogen, nitro, amino, hydroxy, lower alkyl, lower alkoxy or acylamino, X is

n is an integer of 1 or 2 and
A is a group of the formula:

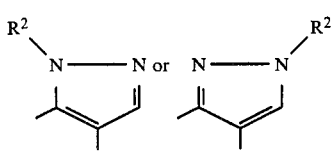

in which
R$^2$ is hydrogen, lower alkyl, lower alkynyl, carboxy(lower)alkyl or protected carboxy(lower)alkyl, or pharmaceutically acceptable salt thereof.

2. A compound of claim 1 in which R$^1$, X and A are each as defined in claim 1 and n is 1.

3. A compound of claim 2 in which R$^1$, X and n are each as defined in claim 2 and R$^2$ is hydrogen, lower alkyl, lower alkynyl, carboxy(lower)alkyl or esterified carboxy(lower)alkyl.

4. A compound of claim 3 in which X and n are each as defined in claim 3 and R$^1$ is halogen, nitro, amino, hydroxy, lower alkyl, lower alkoxy or lower alkanoylamino and R$^2$ is hydrogen, lower alkyl, lower alkynyl, carboxy(lower)alkyl or lower alkoxycarbony(lower)alkyl.

5. A compound of claim 4, in which X and n are each as defined in claim 4, R$^1$ is chlorine, nitro, amino, hydroxy, methyl, methoxy or acetamido and R$^2$ is hydrogen, methyl, isopropyl, propargyl, carboxymethyl or ethoxycarbonylmethyl.

6. A compound of claim 4, which is a compound of the formula:

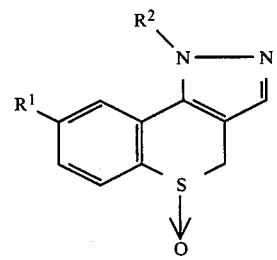

wherein R$^1$ is halogen and R$^2$ is hydrogen or lower alkyl or pharmaceutical acceptable salt thereof.

7. 8-chloro-1,4-dihydro[1]benzothiopyrano[4,3-c]pyrazole 5-oxide or pharmaceutically acceptable salt thereof.

8. 8-chloro-1,4-dihydro-1-methyl[1]benzothiopyrano[4,3-c]pyrazole 5-oxide or pharmaceutically acceptable salt thereof.

9. A pharmaceutical composition having diuretic activity comprising an effective amount of the compound as claimed in claim 7, or pharmaceutically acceptable salt therof, in admixture with a pharmaceutically acceptable carrier.

10. A pharmaceutical composition having uricosuric activity comprising an effective amount of the compound as claimed in claim 7, or pharmaceutically acceptable salt thereof, in admixture with a pharmaceutically acceptable carrier.

11. A pharmaceutical composition having antihypertensive activity comprising an effective amount of the compound as claimed in claim 7, or pharmaceutically acceptable salt thereof, in admixture with a pharmaceutically acceptable carrier.

12. A pharmaceutical composition having diuretic activity comprising an effective amount of the compound as claimed in claim 8, or pharmaceutically acceptable salt therof, in admixture with a pharmaceutically acceptable carrier.

13. A pharmaceutical composition having uricosuric activity comprising an effective amount of the compound as claimed in claim 8, or pharmaceutically acceptable salt thereof, in admixture with a pharmaceutically acceptable carrier.

14. A pharmaceutical composition having antihypertensive activity comprising an effective amount of the compound as claimed in claim 8, or pharmaceutically acceptable salt thereof, in admixture with a pharmaceutically acceptable carrier.

15. A method of treatment of a subject requiring a diuretic agent, uricosuric agent or antihypertensive agent which comprises administering to said subject in need of said treatment an effective amount of compound I, or pharmaceutically acceptable salt thereof, compound I being of the formula:

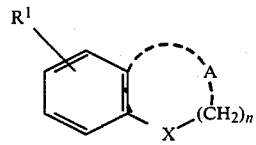

wherein
R¹ is halogen, nitro, amino, hydroxy, lower alkyl, lower alkoxy or acylamino,
x is -S-,

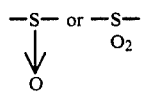

n is an integer of 1 or 2 and
A is a group of the formula:

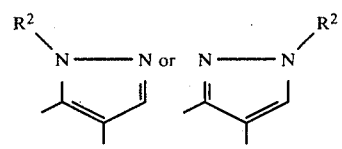

in which
R² is hydrogen, lower alkyl, lower alkynyl, carboxy(lower)alkyl or protected carboxy(lower)alkyl, or pharmaceutically acceptable salt thereof.

16. A method of treatment of a subject requiring a diuretic agent, uricosuric agent or antihypertensive agent which comprises administering to said subject in need of said treatment an effective amount of the compound as claimed in claim 7, or pharmaceutically acceptable salt thereof.

17. A method of treatment of a subject requiring a diuretic agent, uricosuric agent or antihypertensive agent which comprises administering to said subject in need of said treatment an effective amount of the compound as claimed in claim 8, or pharmaceutically acceptable salt thereof.

* * * * *